United States Patent [19]
Razdolsky et al.

[11] Patent Number: 5,622,493
[45] Date of Patent: Apr. 22, 1997

[54] MANDIBULAR DISTRATION DEVICE FOR USE IN MANDIBULAR DISTRACTION OSTEOGENESIS

[76] Inventors: Yan Razdolsky, 600 Lake Cook Rd., Suite 150, Buffalo Grove, Ill. 60089; Patrick J. Driscoll, 203 E. Olive, Prospect Heights, Ill. 60070

[21] Appl. No.: 606,039

[22] Filed: Feb. 22, 1996

Related U.S. Application Data

[63] Continuation-in-part of Ser. No. 222,579, Apr. 4, 1994.
[51] Int. Cl.⁶ ........................................ A61C 3/00
[52] U.S. Cl. ........................................ 433/7; 433/18
[58] Field of Search .................... 433/7, 18, 24

[56] References Cited

U.S. PATENT DOCUMENTS

| | | | |
|---|---|---|---|
| 4,017,973 | 4/1977 | Nelson | 433/18 |
| 4,571,178 | 2/1986 | Rosenberg | 433/7 X |
| 4,676,745 | 6/1987 | Zurita | 433/7 X |
| 4,976,614 | 12/1990 | Tepper | 433/18 |

*Primary Examiner*—Nicholas D. Lucchesi
*Attorney, Agent, or Firm*—Wenderoth, Lind & Ponack

[57] ABSTRACT

A mandibular distraction device for use in distracting the mandible subsequent to corticotomy thereof includes first and second sets of crowns adapted to be attached to the bicuspid and molar teeth of respective opposite lateral sides of the mandible. A first pair of expander assemblies are removably or fixedly attachable to the opposite sides of the first set of crowns, and a second pair of expander assemblies are removably or fixedly attachable to the opposite sides of the second set of crowns. Each pair of expander assemblies includes one expandable device and one sliding tube assembly. Receptors are provided to be attached to the bicuspid crowns and the molar crowns, and corresponding connectors are provided to be attached to the screw devices and sliding tube assemblies for connection thereof to the crowns.

23 Claims, 9 Drawing Sheets

MANDIBULAR DISTRATION DEVICE FOR USE IN MANDIBULAR DISTRACTION OSTEOGENESIS

This application is a continuation-in-part of U.S. patent application Ser. No. 08/222,579, filed Apr. 4, 1994, in the name of Yan Razdolsky, now pending.

BACKGROUND OF THE INVENTION

The present invention relates generally to the correction of deficiencies in mandibular growth. More specifically, the present invention relates to a device for mandibular distraction osteogenesis the (lengthening of the lower jaw by stretching) for correcting deficiencies in mandibular length.

Deficiencies in mandibular growth which lead to characteristic protrusions of the maxillary teeth and deficiencies of the chin are quite common in American and Northern European populations. Data from recent large scale U.S. Public Health Service surveys of the occlusion of children and youth ages 6 through 10 indicate that about 20 percent of the U.S. population has mandibular deficiency, and about 5 percent of the total U.S. population has skeletal mandibular deficiency (deficiency in the growth of the lower jaw) so severe that the only way to correct such deficiency is to perform a total mandibular (lower jaw) resection (osteotomy) and to advance the lower jaw to a more favorable forward position.

A total mandibular osteotomy, or a sagittal split osteotomy, is a major surgical procedure that can have many complications. In this procedure, as illustrated in FIG. 1, a human mandible is split at opposite points on the mandible. The forward part of the mandible is then brought apart from the rearward part and stabilized with either: (1) screws at point S as labeled in the figure (the forward part F is indicated in FIG. 1 by the arrows A as having been moved; this procedure is used less commonly now than in previous years due to the inherent difficulty in positioning of three loose parts of the mandible correctly during the surgery) or (2) splinting of the broken lower jaw to a prefabricated interocclusal splint which is secured to the upper jaw and allowing it to heal for approximately 2 months (during which the patient cannot open his/her mouth, cannot communicate or function and is fed through a straw).

This procedure cuts the bone marrow, and thus could be detrimental to the inner nerves and blood vessels of the mandible.

In addition, a total mandibular osteotomy can involve the complications of bleeding, obstruction of the airway, possible infection, neurological problems such as possible paralysis of the inferior alveolar nerve and loss of sensation to the lip, failure of intermaxillary fixation (stabilization of the mandible after surgery), relapse-movement of the lower jaw in the direction from which it was advanced, and possible displacement of the temporo-mandibular jaw joints during the surgery.

Needless to say, such surgery requires a hospital stay, is very expensive and many patients are reluctant to agree to this. Further, total treatment time is on the order of 30 months.

The other 15 percent of mandibular deficiencies are less severe, and if they are caught early, during the pubertal growth stage, are amenable to conventional orthodontics (braces) or a combination of orthodontics and functional appliance treatment. However, functional appliances are of most benefit to a patient when the patient is undergoing body and jaw growth, and cannot benefit adult (non-growing) patients.

One other prior art surgical technique bears mention. A process of lengthening human long bones (limbs, arms, etc.) by distraction osteogenesis has been utilized for the past 40 years. This process was designed by a Russian surgeon, Dr. Gavriel A. Ilizarov. The principles of the method of Dr. Ilizarov are presented in an article based on a speech delivered by Dr. Ilizarov on Oct. 30, 1987 at the annual Scientific Program of the Alumni Association and material presented by Dr. Ilizarov at a three day international conference on the Ilizarov techniques for the management of difficult skeletal problems. His technique is being widely used by orthopedic surgeons throughout the United States and the world.

SUMMARY OF THE INVENTION

The object of the present invention is to provide an appliance or device for distraction osteogenesis that is applicable to the five percent of severe cases requiring surgery as well as to the less severe 15 percent of cases if those cases have missed their opportunity for orthodontic/functional correction during their pubertal growth years. Distraction osteogenesis is, by definition, the process of generating new bone by stretching. Thus, it is the more specific object of the present invention to provide a device for generating new mandibular bone by stretching the mandible, while orthodontically lengthening the mandible and minimizing the extent of the conjunctive lower jaw surgery.

The objects of the present invention are met by a device used in a method of mandibular distraction osteogenesis. This method involves performing corticotomy surgery, where only the cortex of the mandible is cut, leaving all bone marrow, nerve and blood vessels intact, at two points on opposite sides of the mandible. The device is an expandable distraction device attached to the teeth of the mandible on opposite sides of the two points of the corticotomy surgery, and the expandable distraction device is then periodically expanded until a desired mandibular length is attained.

The method further comprises preparing the expandable distraction device for attachment during the corticotomy surgery. This includes fitting a plurality of stainless steel crowns onto the teeth of the mandible, taking an impression of the teeth of the mandible, removing the crowns from the teeth of the mandible and placing the crowns in the impression, preparing a solid model of the teeth of the mandible from the impression, the crowns being located on the solid model, and then attaching the expansion screw devices to the crowns.

Preferably, two expansion screw devices and two sliding tube devices are attached to eight crowns fitted onto the teeth of the mandible in the step of fitting, including two bicuspid and two molar crowns on each side of the mandible.

The impression is preferably a rubber base impression that is poured up with dental stone or plaster. The expansion screw devices and sliding tube devices are preferably soldered to the crowns by means of sliding (removable) attachments, in a very precise three dimensional location.

The expandable distraction device is subsequently expanded in the desired direction of the distraction of the mandible. The screw devices separate the crowns on each side of the mandible from each other at the point of the corticotomy surgery on the mandible. Preferably, the expandable screw devices are expanded at a rate of 1 mm per day, starting the day of the surgery.

The objects of the present invention are thus met by the provision of a mandibular distraction device having first and second sets of tooth crowns (or possibly bands), a first set of expandable screw and tube devices connected to the first set of tooth crowns and a second set of expandable screw and tube devices connected to the second set of tooth crowns.

Each expandable screw device preferably comprises first and second body portions that have aligned threaded holes extending therein and a threaded shaft engaging both of the threaded holes.

Further, each set of tooth crowns is preferably disposed along a respective tooth line, each expandable screw device of each set of expandable screw and tube devices being disposed on a side of the tooth line opposite the other sliding tube of the set. Each set of expandable screw and tube devices is soldered to their respective set of tooth crowns.

Further, each set of tooth crowns preferably comprises a plurality of crowns that are aligned for disposition on the teeth of one side of the mandible. Each screw device has a forward portion that connects to some of the bands on one set of tooth crowns and a rearward portion connected to the remainder of the crowns of the set. The forward and rearward portion are thus expandable relative to each other for separation of the crowns from each other.

Preferably, the first set of tooth crowns, having the first set of expandable screw and tube devices thereon, is connected to the second set of tooth crowns, having the second set of expandable screw and tube devices thereon, at forward portions of the expandable screw devices. If so desired, the forward portions of the expandable screw and tube devices can be connected to each other by heavy gauge stainless steel wire.

More broadly, the mandibular distraction device meeting the objectives of the present invention comprises first and second sets of tooth engagement members that are adapted to be attached to mandibular teeth of respective opposite lateral sides of the mandible, wherein each of the first and second sets of tooth engagement members has opposite sides. A first pair of expander assemblies are attached to the opposite sides of the first set of tooth engagement members, the first pair of expander assemblies comprising at least one expandable screw device. A second pair of expander assemblies is attached to the opposite sides of the second set of tooth engagement members, the second pair of expander assemblies also comprising at least one expandable screw device. The first and second pairs of expander assemblies are preferably removably attached to the opposite sides of the tooth engagement members.

According to a further preferred feature of the present invention, the first and second sets of tooth engagement members have receptors attached thereto, and the first and second pairs of expander assemblies have connectors attached thereto that are removably engageable with the receptors. Each of the receptors preferably comprises a metal member fixed to at least one of the tooth engagement members and has a connector guide extending thereon, and each connector preferably comprises a metal member fixed to one of the extender assemblies and has an engagement surface complementary to the connector guide of a respective one of the receptors for removable engagement therewith.

According to a first preferred embodiment of the present invention, the receptors comprise a back portion fixed to at least one of the tooth engagement members and a front portion defining the connector guide. The connector guide comprises a vertical slot open at front and upper areas thereof, and is closed at the back area and a lower area thereof. The lower area defines a vertical stop, and the slot tapers from the back area adjacent to the back portion toward the front area. The connectors preferably comprise a plug having a front portion fixed to one of the expander assemblies and a plug portion that extends vertically and has a taper complementary to the vertical slot of the at least one of the receptors.

According to a further preferred embodiment of the receptors and connectors of the present invention, the receptors comprise a back portion fixed to at least one of the tooth engagement members and a front portion defining the connector guide. The connector guide comprises a vertically tapering front member having a pair of vertically extending flanges thereon defining spaces between the front portion and the tooth engagement members and a vertical stop. The connectors comprise a cap having a front portion fixed to one of the expander assemblies having a rear surface engageable with the front portion of the at least one of the receptors and channel members on the front portion that extend vertically and have a taper complementary to the vertically tapering front member of the receptors. The front portion is engageable with the vertical stop.

According to the further preferred embodiment of the receptors and connectors, the vertically extending flanges have secondary flanges extending therefrom toward the at least one of the tooth engagement members, thus forming glue pockets that are adapted to receive glue for gluing the cap to the receptor. The receptors may have a vertical alignment hole therein extending from an upper surface thereof. The cap can also have a slot extending horizontally across the front portion thereof at the lower end thereof. The back portion of the receptors can also comprise horizontally extending tabs so as to be fixable to two tooth engagement members.

The receptors and connectors are preferably made of stainless steel and soldered to the tooth engagement members and the expander assemblies. As noted earlier, the tooth engagement members may be stainless steel bands, but according to a preferred feature of the present invention are stainless steel crowns.

Each expandable screw device comprises first and second body portions having aligned threaded holes extending therein in a threaded shaft engaging both of the threaded holes. Each set of tooth engagement members comprises a plurality of members aligned for disposition on the teeth of one side of the mandible, and each expandable assembly comprises a forward portion connected to some of the members of one set of tooth engagement members and a rearward portion connected to the remainder of the members of the one set of tooth engagement members. The forward and rearward portions are expandable relative to each other for separation of some of the members from the remainder of the members. The first set of tooth engagement members having the first pair of expandable assemblies thereon are connected to the second set of tooth engagement members having the second pair of expandable assemblies thereon at forward portions of the expandable assemblies. The forward portions can be connected by a further expandable assembly, or, as noted above, by heavy gauge stainless steel wire.

The tooth engagement member is comprised of bicuspid and molar engagement members. The receptors preferably include bicuspid receptors attached to the bicuspid engagement members and molar receptors attached to the molar engagement members.

One of the bicuspid receptors, according to a further preferred embodiment of the present invention, may comprise a front portion defining a connector guide, the connector guide comprising a pair of vertically extending flanges, a vertical stop on the front portion, an intermediate portion extending from the front portion and a back portion extending from the intermediate portion. The intermediate portion spaces the back portion from the front portion, and the back portion is connected with two of the bicuspid engagement members. The molar receptors preferably comprise a back portion that is fixed to two of the molar engagement members and a front portion defining the connector guide, the connector guide having a pair of vertically extending flanges thereon and a vertical stop. The connectors comprise a cap having a front portion fixed to one of the expander assemblies, the rear surface engageable with the front portion with the at least one of the receptors and channel members on the front portion for engagement with the flanges, the front portion also being engageable with the vertical stop.

According to the present invention, the invention also contemplates an assembly kit made up of the components described above for constructing a mandibular distraction device, it being understood that the mandibular distraction device is a custom made device made by a doctor from the components for a particular patient for the purposes of conducting the above-described procedure.

Through the employment of mandibular distraction osteogenesis according to the present invention, and the use of the mandibular distraction device according to the present invention, a number of significant advantages may be achieved. As noted above, the invention will orthodontically lengthen the mandible while minimizing the extent of the conjunctive lower jaw surgery. Only corticotomy is employed.

Further, the invention will improve the facial profile by advancing or lengthening the deficient mandible. This will improve the lip balance, lip competence, and lip seal. This will also help to eliminate mouth breathing pattern problems. Further, incisor guidance and function will be established.

The invention will also reduce the orthodontic-surgical treatment time. Treatment time can be expected to be reduced to on the order of 12 months, instead of 30 months as with the prior art sagittal split osteotomy surgery.

The invention will also bring the mandible forward, thus bringing the tongue forward and diminishing chances for obstructive sleep apnea or snoring. Such correction will also help to prevent class II mandibular deficiency/malocclusion. The invention will help to correct unilateral cross bites and the mandibular midline.

Further, the invention will minimize damage to the periosteal and endosteal blood supply by performing a corticotomy only, rather than a complete osteotomy as is now performed with the sagittal split osteotomy surgery. This will minimize swelling and post-surgical complications, and requires no hospital stay and could be done on an outpatient basis. Furthermore, the fact that the expansion screw assemblies are detachable from the receptor assemblies means that the orthodontist will generally not need to be present during surgery. The precise pre-alignment will have been done during fitting in the office.

Further, the procedure will be far less expensive than the conventional mandibular osteotomy surgery. Patient costs for the procedure are lower than the costs associated with prior art methods such as the sagittal split osteotomy surgery. Obviously this will tend to lower health care costs in general, which is a great concern at this time.

Other significant advantages result to the benefit of the patient. The procedure according to the present invention results in less pain to the patient than the prior art procedure. The recovery period after completion of the procedure is on the order of two to three days, rather than two months as with other methods. The jaw of the patient does not have to be wired shut for two months, and the patient is able to return to work within one week, as opposed to eight weeks with other methods. Thus it is clear that the psychological impact of the procedure on the patient will be significantly reduced as compared with the impact of the prior art methods.

BRIEF DESCRIPTION OF THE DRAWINGS

The present invention will be described in detail below with reference to the accompanying drawings, in which.

DETAILED DESCRIPTION OF THE PREFERRED EMBODIMENTS OF THE INVENTION

Figure 1:
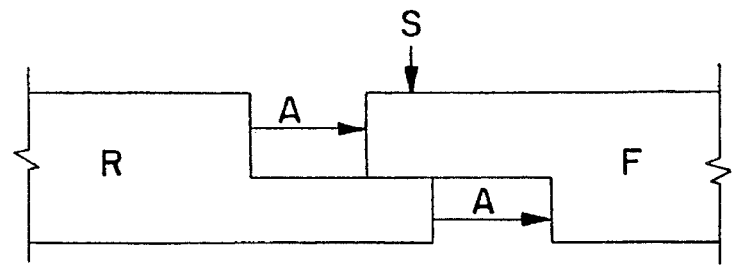
FIG. 1 is a schematic drawing illustrating sagittal split osteotomy surgery.

A detailed description of the present invention will now be presented with reference to the accompanying drawing figures. In the various figures, the same reference numerals are used for similar elements throughout. The description of the invention will proceed with the description of a mandibular distraction osteogenesis device and in particular Razdolsky attachments for the purpose of securing expansion screws and sliding tubes onto the stainless steel crowns in a precise angular fashion and making both expansion screws and sliding tubes removable prior to corticotomy surgery.

Figure 2:
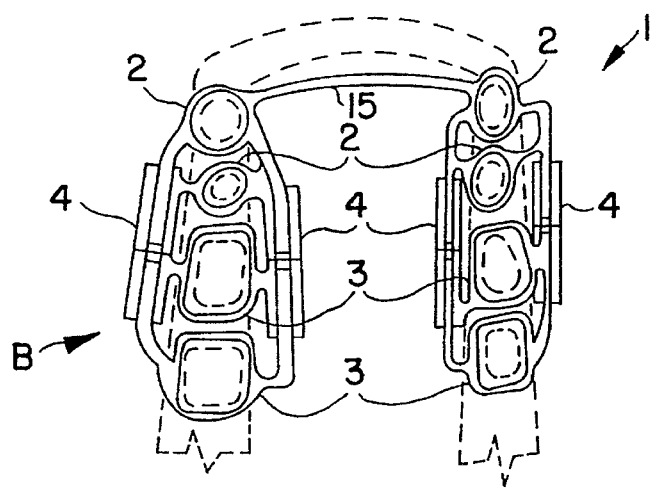
FIG. 2 is a top view of a mandibular distraction osteogenesis device according to the present invention.
Figure 3:
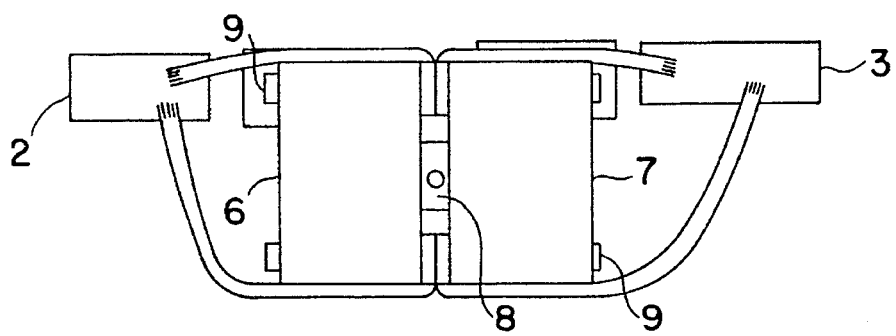
FIG. 3 is a side view of a portion of the mandibular distraction device as seen in the direction of arrow B of FIG. 2.

Turning to FIG. 2, there is illustrated a mandibular distraction osteogenesis device 1 usable in distracting the mandible. Initially, the device 1 includes a plurality of crowns (or bands, collectively also referenced as tooth engagement members) for placement on the teeth of the mandible of a patient that is to undergo distraction osteogenesis. The tooth engagement members of the present invention are preferably crowns, but it should be recognized that bands could also be employed instead of crowns; the description will primarily discuss crowns. In FIGS. 2 and 3, while the description references crowns, the illustration in these figures is not meant to be indicative of any particular type of crown but to be simply a generic description of a crown or band for purposes of illustrations.

Preferably there are provided a total of eight crowns, with two bicuspid and two molar orthodontic crowns being provided for each side of the mandible, as illustrated in FIG. 2. The crowns are indicated by reference numbers 2 for the bicuspid crowns and reference numbers 3 for the molar crowns. The mandible and the relevant teeth are schematically illustrated by a dashed line in FIG. 2.

One universal expansion screw 4 is soldered onto each buccal (cheek) side of the crowns and one universal sliding tube device 5 is soldered onto each lingual (tongue) side of the crowns for each side of the mandible. One universal expansion screw 4 and one sliding tube 5 is thus placed on each side of each set of crowns. As can be seen from FIG. 2, the universal expansion screws thus extend along the sides of the crowns and have suitable portions thereof soldered to the respective crowns. The universal expansion screws 4 are expandable to distract a forward portion of the mandible, the upper portion as seen in FIG. 2, from a rearward portion of the mandible by separating the bicuspid bands 2 from the molar bands 3.

More specifically, and referring to FIG. 3, each universal expansion screw 4 has two halves 6 and 7 separable from each other by a screw mechanism 8. The screw mechanism 8 is a suitable mechanism rotatable between the universal expansion screw halves 6 and 7 to separate the halves from each other, such as a right and left hand threaded shaft extending into and engaging with corresponding threads in the halves 6 and 7. Suitable guide rods 9 can also extend through the halves 6 and 7 to guide the separation of the halves 6 and 7 from each other. As can be seen, suitable connecting portions are provided for connecting the halves 6 and 7 to the respective bands 2 and 3. Such connecting portions can take the form of appropriate metal wires or bars. The universal expansion screw 4 can be of the type illustrated in U.S. Pat. No. 4,482,318, for example, or could be of the type shown in U.S. Pat. No. 4,571,177, suitably adapted to the present situation. These patents are incorporated herein by reference.

By the above construction there is formed two separate portions of the mandibular distraction device 1, one portion being located on each side of the mandible. These portions are preferably connected to each other by a suitable connecting wire or bar 15, as illustrated in FIG. 2. However, note that in place of the connecting wire or bar 15, an additional, smaller, universal expansion screw 4 could be provided and incorporated into the device 1, the universal expansion screw connecting the two sides of the device 1 at the forward portions thereof in order to allow for lateral mandibular expansion, in addition to mandibular distraction or elongation.

As can be seen from FIG. 2, the bicuspid crowns 2 on each side of the mandible are connected to the forward portions or halves 6 of the universal expansion screws 4, and the molar crowns 3 are connected to the rear portions or halves 7 of the universal expansion screws 4. Thus, a unitary forward portion is expansible in a forward direction relative to two separate lateral portions on opposite sides of the mandible for elongation or distraction of the mandible.

Though not specifically illustrated, the sliding tubes 5 represent simple expandable sliding tube and pin connections connecting the forward and rearward portions of the device 1 on each side of the mandible. These tube and pin connections have a simple tube receiving a pin with the tube connected to one portion and the pin connected to the other portion and extending in the same direction as the expansion screws 4. Thus these devices will simply follow the distraction of the mandible along with the activation of the screw devices 4, but will provide for support on the lingual side of the crowns in all directions except for the direction of expansion. Such sliding tubes, as well as the expansion screws and crowns, are separately readily available from orthodontic suppliers.

While the above described distraction device 1 simply solders the expansion screws and sliding tubes 5 to the crowns 2 and 3, it is preferred that specific attachments be employed for this purpose, as will be described below. These attachments, generally referred to as Razdolsky attachments, comprise receptor attachments attached to the respective crowns, preferably by soldering, and connector attachments connected to the respective screw devices and sliding tubes 5 also by soldering. The receptors and connectors are thus removably engageable with each other so that they screw devices 4 and sliding tubes 5 can be removably attached to the crowns, for reasons as will be discussed below in describing the method of mandibular distraction osteogenesis in accordance with the device of the present invention. At this point, specific description of the Razdolsky attachments will be made.

Figure 5:
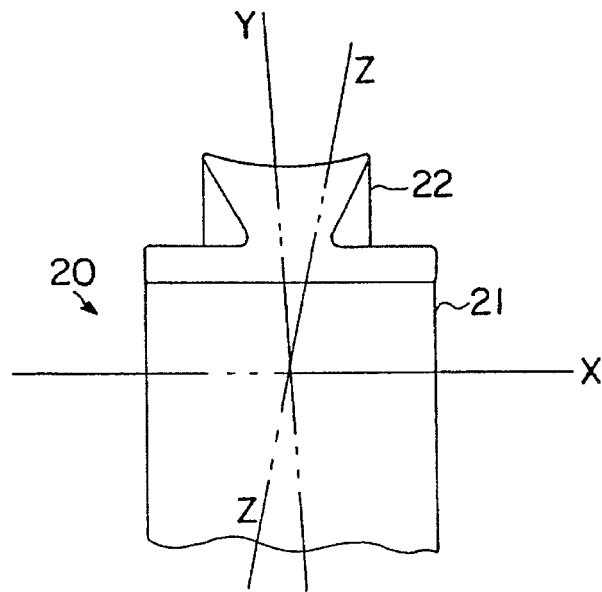
FIG. 5 is a partial perspective view of a Razdolsky attachment plug according to a first embodiment of attachments for the mandibular distraction device according to the present invention.
Figure 6:
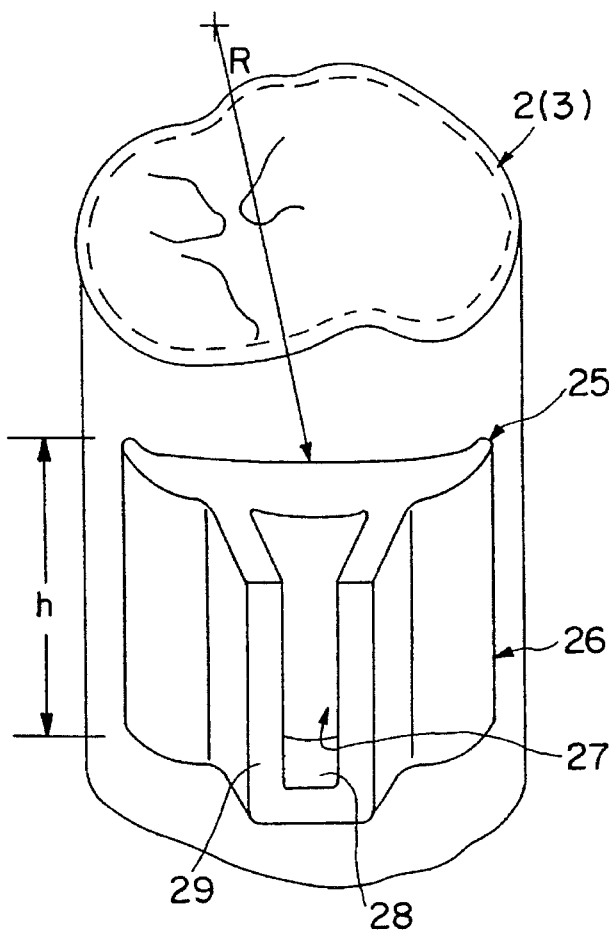
FIG. 6 is a perspective view of a receptor according to the first embodiment of the Razdolsky attachments, the receptor being mounted on a crown.
Figure 7:
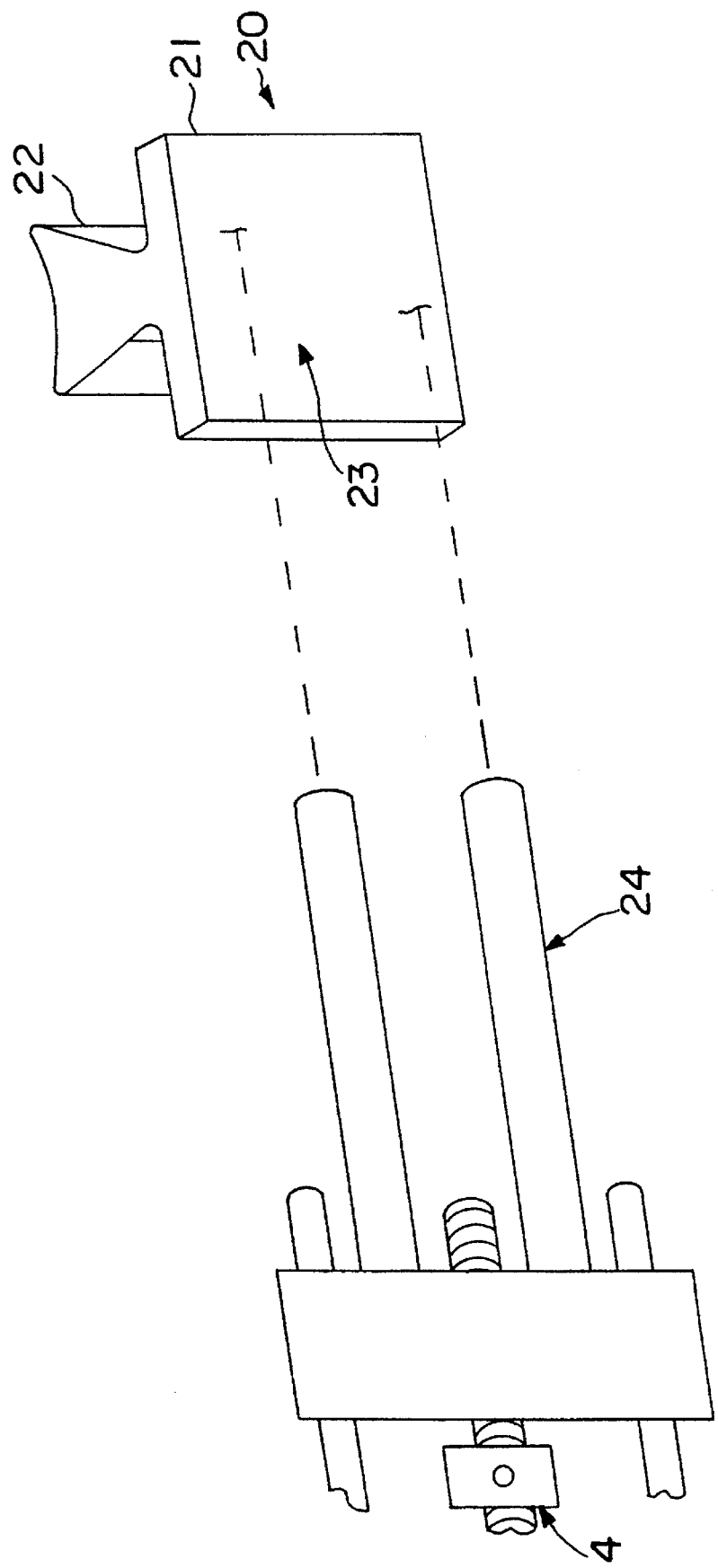
FIG. 7 is an exploded view of the plug and a screw device according to the first embodiment of the Razdolsky attachments.

A first embodiment of the Razdolsky attachments is illustrated in FIGS. 5–7. FIG. 5 illustrates a plug attachment for attachment to a screw device 4, FIG. 6 illustrates a crown 2 or 3 having a connector 25 connected therewith and FIG. 7 illustrates a connection between the screw device 4 and the plug 20.

The attachment plug 20 according to the Razdolsky attachments comprises a front portion 21 having a front surface and a plug portion 22. The plug portion 22 tapers from its distal end in the Z direction to the front portion 21, as illustrated.

FIG. 6 illustrates a stainless steel crown 2 or 3, preferably a stainless deep drawn thin shell molar or bicuspid cap as are commercially available. The receptor 25 is soldered to the stainless steel cap, and is preferably itself an investment cast stainless steel, etc. Solder flow details are provided on each side as illustrated at 26, noting the beads on the vertical sides of the receptor 25. The majority of the receptor 25 comprises the back portion soldered to the cap. A slot 27 is formed by a front portion 29, which has outwardly jutting walls defining the slot 27 as a slot tapering from the back portion toward the front. The slot is opened at its top and forward sides, and is closed at the back and lower portions thereof. The lower portion at 28 forms a vertical stop.

As seen in FIG. 7, expansion device solder legs 24 of the screw device 4 can be soldered to the front portion 21 of the plug 20 as noted at 23, designating a solder surface on the plug 20. During assembly, the plug 20 can then have its plug portion 22 vertically inserted into the slot 27 of the receptor 25, the plug 22 being complementary to the slot 27 for a snug fit. The plug 22 can be a solder plug and can provide a snug fit with a very low viscosity adhesive joint in the receptor 25.

The receptor 25 has a height h and a radius of its back surface R. The receptor 25 can thus be provided in several general ranges of sizes for general ranges of the sizes of teeth.

Figure 8:
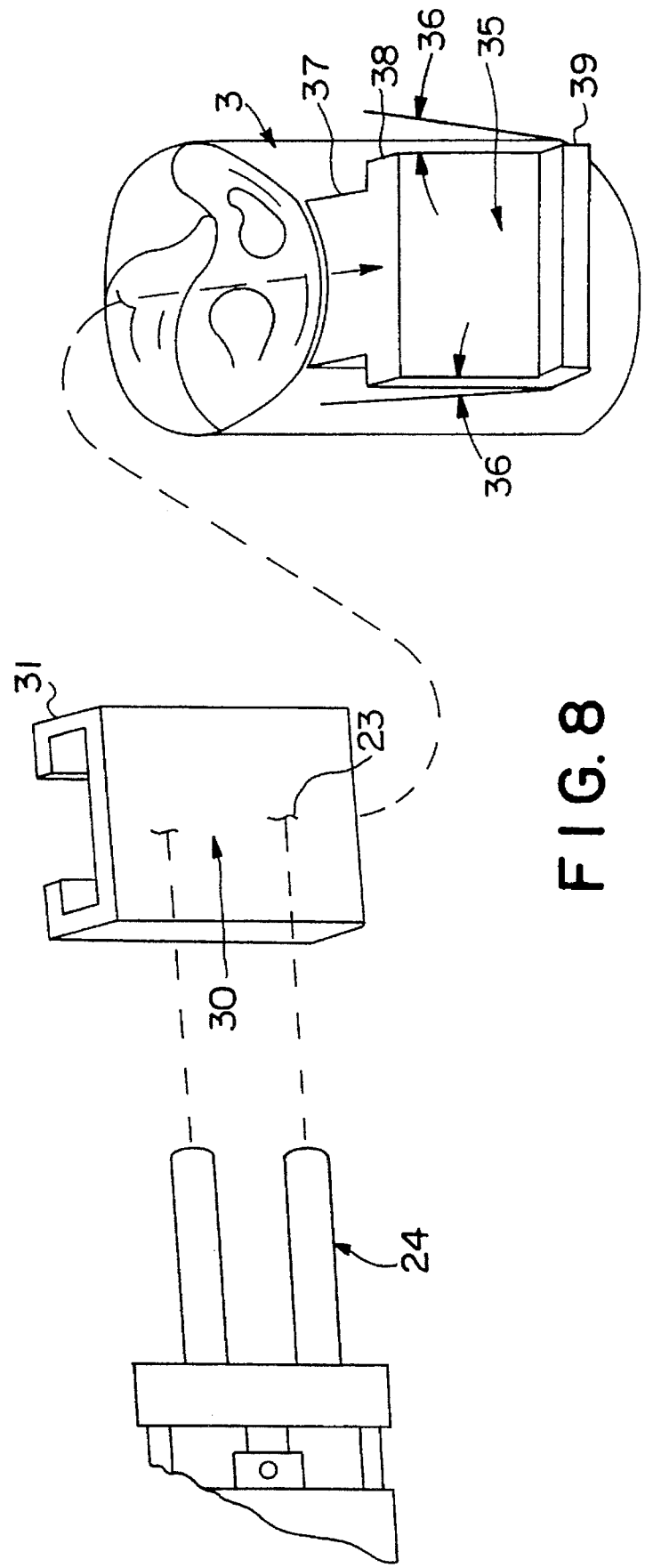
FIG. 8 is an exploded view of a screw device, a cap and a receptor according to a second embodiment of the Razdolsky attachments according to the present invention.

A second embodiment of the Razdolsky attachments is illustrated by FIG. 8. In this figure, the attachments comprise a cover or cap 30 in place of the plug, and a receptor 35. The receptor 35 is illustrated as attached to a molar crown 3, for example by soldering. The receptor 35 has a front portion 38 having lateral flanges with respect to the back portion 37 that is connected to the crown 3. The flanges have a slight taper shown at 36. The cap or cover 30 has flanges or channel members 31 forming channels for engagement with the flanges of the front portion 38. When engaged as illustrated, the slight taper wedges the cap or cover 30 in place, and the cap 30 engages a vertical stop 39 on the bottom of the receptor 35.

Figure 9:
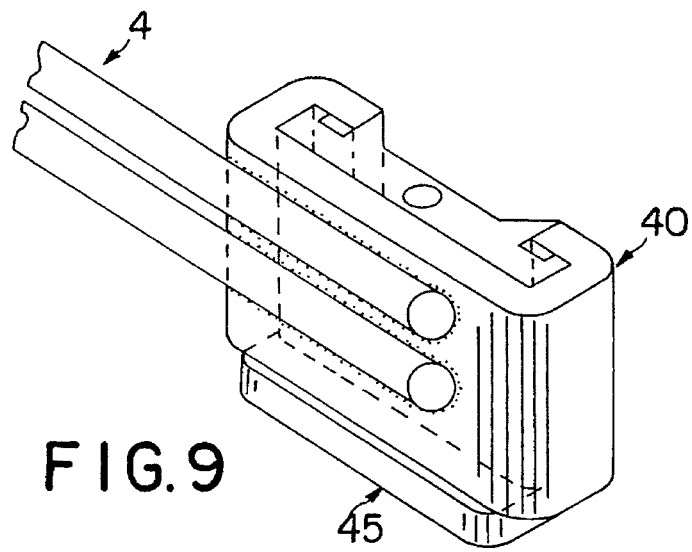
FIG. 9 is a perspective view of a cap and a receptor according to a third embodiment of the Razdolsky attachments of the present invention.
Figure 10:
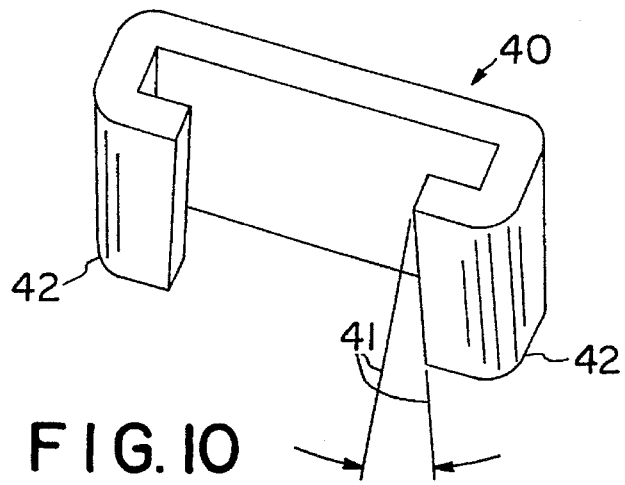
FIG. 10 is a perspective view of the cap of FIG. 9.
Figure 11:
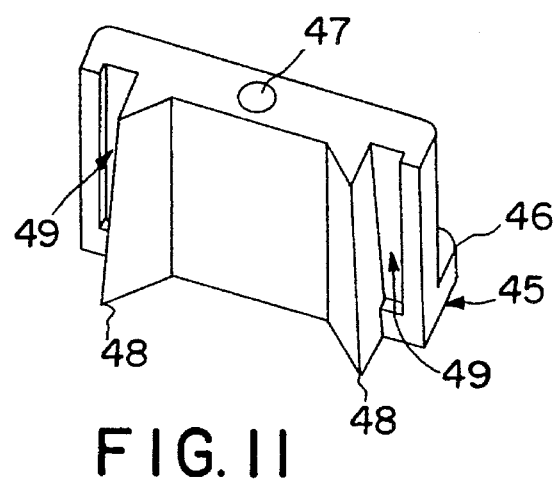
FIG. 11 is a perspective view from the rear of the receptor of FIG. 9.

FIGS. 9-11 illustrate a third embodiment according to the Razdolsky attachments of the present invention. In this embodiment, the cap 40 engages a receptor 45. The receptor 45 has a vertical stop 46 similar to the above embodiments, and an alignment hole 47. The cap 40 has channels 42 for engaging the rear surface of the receptor 45, with the turned flanges of the channels 42 having a taper at 41. The taper is provided for a tight fit against triangular engagement members 48 on the receptor 45, which are similarly tapered. According to a particular feature of this embodiment, glue pockets 49 are provided on the back surface of the receptor 45 for gluing the cap 40 to the receptor 45 during surgery.

Figure 12:
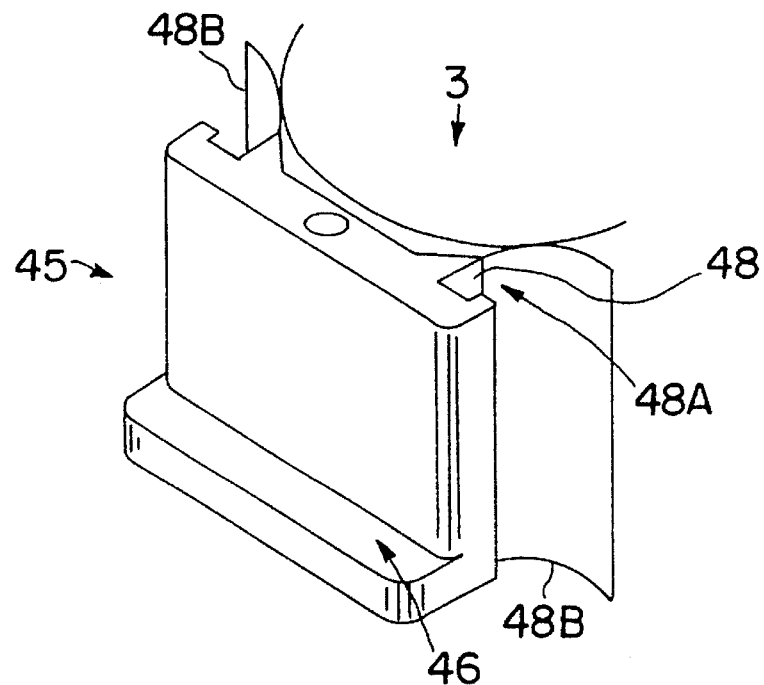
FIG. 12 is a perspective view of a receptor according to a modification of the third embodiment of the Razdolsky attachments.

In a variation of the third embodiment illustrated in FIG. 12, bendable wings 48b can be soldered at 48a to the rear engagement portions 48 of the receptor 45. These bendable wings can engage a molar cap 3.

Figure 13:
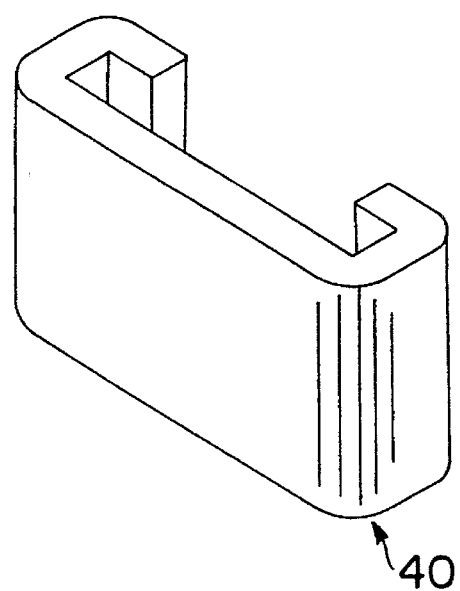
FIG. 13 is a perspective view of a cap suitable for use with the receptor of FIG. 12.

FIG. 13 provides a front perspective view of the cap 40 according to the third embodiment of the Razdolsky attachments of the present invention.

Figure 14:
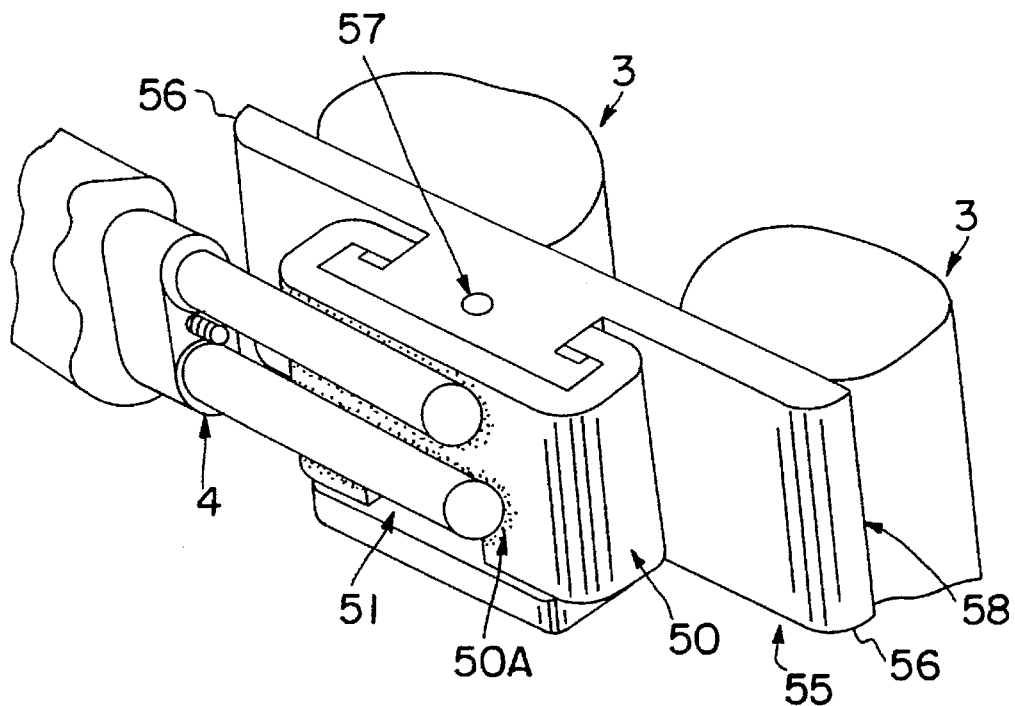
FIG. 14 is a perspective view of a screw device, cap and receptor according to a fourth embodiment of the Razdolsky attachments of the present invention.
Figure 15:
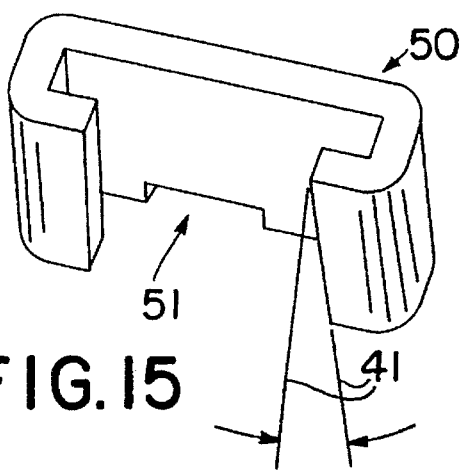
FIG. 15 is a perspective view of the cap of FIG. 14.
Figure 16:
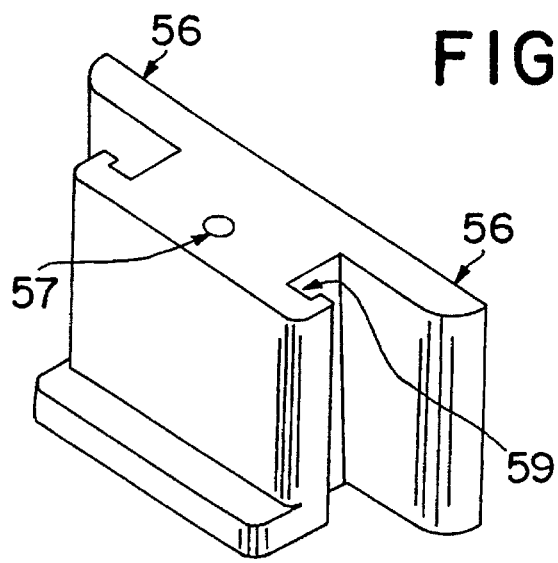
FIG. 16 is a perspective view of the receptor of FIG. 14.

FIGS. 14-16 describe a fourth embodiment of the Razdolsky attachments according to the present invention. A cap 50 is similar to the cap discussed with respect to the third embodiment of the Razdolsky attachments and is connected to the screw device 4 in a similar manner. However, in this embodiment a slot 51 is provided in the cap for receipt of a pry bar for removal of the cap from the receptor during an intermediate step of the procedure. It will be recognized that the slot could be provided with the other embodiments of the connectors of the present invention. A receptor 55 of this embodiment is similar to the receptor of the third embodiment of the Razdolsky attachments in that it has a similar front portion providing a vertical stop and an alignment hole 57, and provides similar glue pockets at the rear surface of the front portion. However, with this embodiment the rear portion is extended further back and connected with two laterally extending tabs 56 so that the single receptor 55 may be connected with two molar caps 3 as illustrated in FIG. 14. As seen at 58, the tabs 56 are soldered to the stainless steel caps. Thus employment of this embodiment will reduce the number of receptors and caps necessary for connection of the expansion screw devices 4 and sliding tube devices 5 on the sides of the lines of crowns. This will be further discussed below.

Figure 17:
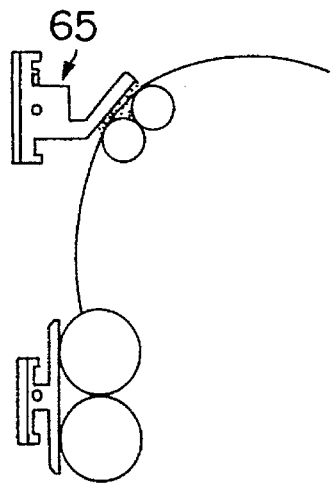
FIG. 17 is a schematic view of a receptor according to the fourth embodiment of the Razdolsky attachments used together with the receptor according to a fifth embodiment of the Razdolsky attachments of the present invention.
Figure 18A:
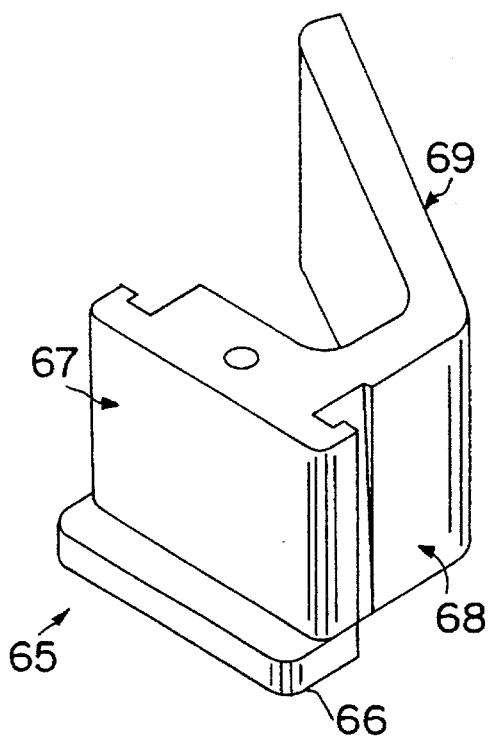
FIG. 18A is a perspective view of the receptor according to the fifth embodiment of the Razdolsky attachments.
Figure 18B:
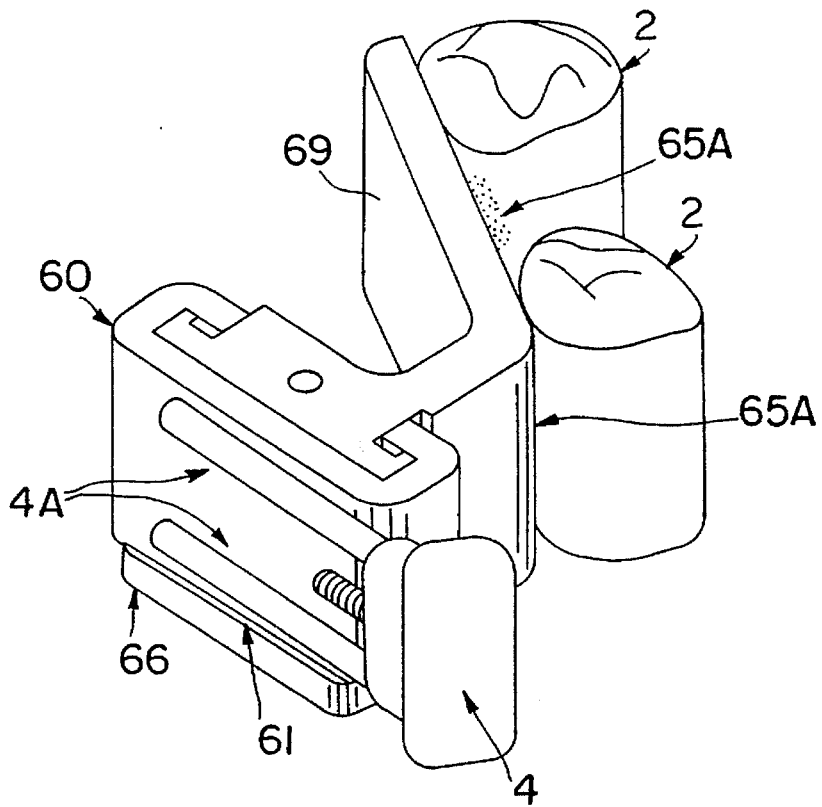
FIG. 18B is a perspective view of a screw device, cap and receptor according to the fifth embodiment.

FIGS. 17-18B illustrate a fifth embodiment of the Razdolsky attachments according to the present invention, and can be used together with the fourth embodiment. That is, in this embodiment a receptor 65 has a front portion 67 with a vertical stop 66 similar to that of the third and fourth embodiments. However, instead of having the laterally extending tabs of the fourth embodiment, an intermediate portion 68 extends rearwardly from one side of the rear surface of the front portion 67, and continues into a back portion 69 that extends from the intermediate portion 68 at an angle that is acute relative to the direction of the expander assemblies. The cover 60 is similar to the previous embodiments and is provided with a pry slot 61 for engagement by a suitable tool, such as a thin bladed screwdriver, etc. As illustrated in FIG. 18B, the back portion 69 is soldered at 65a to two bicuspid crowns 2. The angle of the portion 69 allows the front 67 to be better aligned with respect to the assembly of the screw device 4 with its respective caps soldered thereto. In this regard, note FIG. 17. In this figure, two bicuspid caps are seen as connected with the receptor 65 and two molar caps are seen as connected with the receptor 55 according to the fourth embodiment. As seen in the figure, by the angled rear portion 69 of the receptor 65, both the front portions of the respective receptors can be aligned with reach other, making the process of assembly a simple matter.

With respect to the fifth embodiment, the bicuspid receptor 65 that is illustrated in FIG. 18A is obviously only usable on one side of the distraction device, i.e. on one side of the mandible. However, it is contemplated that a symmetric bicuspid receptor could be manufactured that would be usable on both sides of the mandible so that only one part would have to be manufactured.

Figure 4:
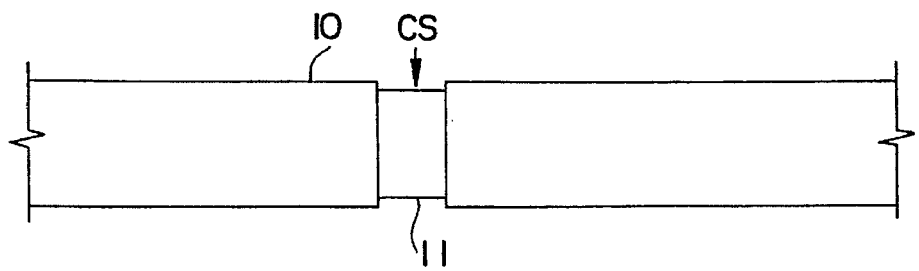
FIG. 4 is a schematic representation of corticotomy surgery.

The method of mandibular distraction osteogenesis according to the present invention is as follows. Referring to FIGS. 2-4, first two bicuspid and two molar orthodontic crowns are fitted onto the respective teeth of a patient's mandible on each side of the mandible. Thus, a total of eight crowns are fitted onto the teeth of the patient. A rubber base impression is then taken of the patient's mandible with the crowns in place. The crowns are then removed and placed into the impression. Then, the impression is poured up with orthodontic (dental) stone or plaster, so as to form a model of the patient's mandible, with the crowns in place thereon on the appropriate teeth of the mandible model.

Figure 19A:
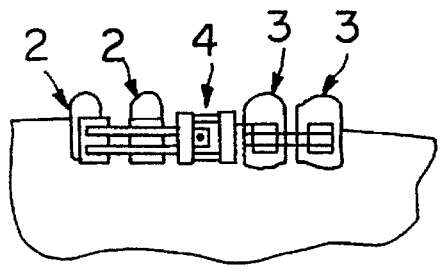
FIGS. 19A–19D are illustrations of steps in the process of using the present invention.

The two universal expansion screws 4 are then soldered onto the connectors of the Razdolsky attachments and the receptors are soldered onto the crowns (FIG. 19A) in a very precise angular fashion preferably using the laboratory instrument discussed in U.S. patent application Ser. No. 08/222,579, filed Apr. 4, 1994 (incorporated herein by reference). Two sliding tubes are also soldered onto the crowns 2 and 3 in a simple fashion utilizing the Razdolsky attachments. Thus the mandibular distraction device 1 is formed. A suitable connection 15 (FIG. 2, which shows the embodiment not using the attachments) may also be provided, or an additional universal expansion screw 4 may also be provided in place thereof to provide for lateral mandibular expansion. With the finished mandibular distraction device 1, the device is now ready to be cemented into the patient's mouth.

Figure 19B:
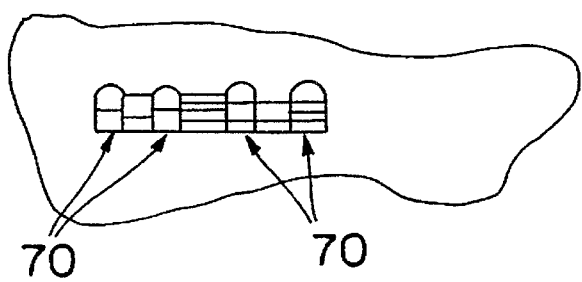
Figure 19C:
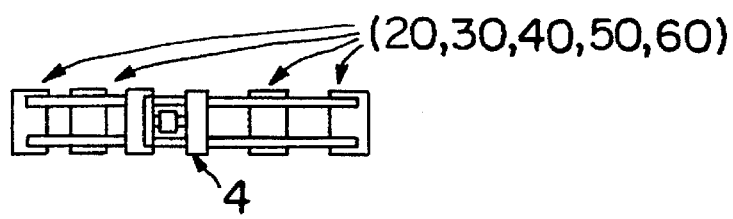
Figure 19D:
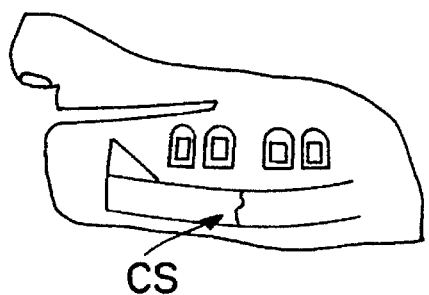

Accordingly, the mandibular distraction device is cemented into the patient's mouth prior to corticotomy surgery as at 70 (FIG. 19B). All expansion screws and sliding tubes are then removed (FIG. 19C) by means of the Razdolsky attachments, which guarantee the previous exact angular positioning, and are only to be reinserted after the corticotomy surgery is performed. When the screw devices and sliding tubes are removed by the use of the Razdolsky attachments, the crowns stay cemented on the patient's teeth. This technique provides for maximum access and visibility during the surgery. Corticotomy surgery is then performed, which is the cutting of the outside layer (cortex) only of the mandible (FIG. 19D). Referring to FIG. 4, a section of the patient's mandible is schematically illustrated. Portion 10 represents the outer layer of the bone, i.e. the cortex. This portion is cut during the corticotomy surgery. However the bone marrow 11 is left intact. This reduces the chance of the nerves or the blood vessels being severed. The location of the corticotomy surgery is represented in FIG. 4 by the letters CS. The corticotomy surgery is performed at two points on opposite sides of the mandible to allow for the elongation or distraction of the forward portion of the mandible from the rearward portion thereof. The corticotomy preferably takes place posterior to the lower second bicuspids, and preferably between the bicuspids and the molars on each side of the mandible to allow for the two bicuspid crowns 2 on each side to be displaced forwardly from the rear molar crowns 3 with the expansion of the universal expansion screws 4. Appropriate x-rays can be taken of the mandible in order to determine the exact thickness of the cortex to ensure that the bone marrow 11 is not cut.

After the reinsertion of the expansion screws and sliding tubes after corticotomy surgery, the mandible is then distracted by expanding the two universal expansion screws 4 inside of the patient's mouth. This is accomplished by rotating the screws 8 of the universal expansion screws 4 periodically to extend the forward portion of the mandible from the rearward portion thereof. This is possible because the cortex has been cut in the corticotomy surgery. The bone marrow is softer tissue and allows for elongation to take place. Both bone and soft tissue regeneration will occur during the process of expanding the universal expansion screws 4 and distracting the mandible. Preferably, the mandible is distracted at a rate of 1 mm per day until the proper mandibular length is obtained. There may be differential expansion between the left and right sides in order to maintain expansion along the centerline of the mandible.

Note that when reinserting the expansion screws and sliding tubes, the respective connectors are connected with the respective receptors. At this time, the receptors and connectors are preferably permanently bonded to each other prior to adjustment of the mandible by a suitable adhesive. However, as an alternative to adhesive, it is contemplated that a locking mechanism could be provided between each connector and receptor. Such a locking mechanism would preferably be of a type in which the receptor and connector are securely fixed with each other, but which could be quickly released by the orthodontist or surgeon, and different types of such locking mechanisms will occur to those of skill in the art.

While preferred embodiments of the present invention have been described above in some particularity, the scope of the present invention should not be limited thereby, as various modifications thereof will be apparent to those of skill in the art.

We claim:

1. A mandibular distraction device, comprising:

first and second sets of tooth engagement members adapted to be attached to mandibular teeth of respective opposite lateral sides of the mandible, wherein each of said first and second sets of tooth engagement members has opposite sides;

a first pair of expander assemblies attached to said opposite sides of said first set of tooth engagement members, said first pair of expander assemblies comprising at least one expandable screw device; and a second pair of expander assemblies attached to said opposite sides of said second set of tooth engagement members, said second pair of expander assemblies also comprising at least one expandable screw device.

2. The mandibular distraction device of claim 1, wherein said first and second pairs of expander assemblies are removably attached to said opposite sides of said sets of tooth engagement members.

3. The mandibular distraction device of claim 2, wherein said first and second sets of tooth engagement members have receptors attached thereto, and said first and second pairs of expander assemblies have connectors attached thereto that are removably engageable with said receptors.

4. The mandibular distraction device of claim 3, wherein:

each of said receptors comprises a metal member fixed to at least one of said tooth engagement members and has a connector guide extending thereon; and each said connector comprises a metal member fixed to one of said expander assemblies and has an engagement surface complementary to said connector guide of a respective one of said receptors for removable engagement therewith.

5. The mandibular distraction device of claim 4, wherein:

at least one of said receptors comprises a back portion fixed to at least one of said tooth engagement members and a front portion defining said connector guide, said connector guide comprising a vertical slot open at front and upper areas thereof and closed at said back area and a lower area thereof, said lower area defining a vertical stop, and said slot tapering from said back area adjacent to said back portion toward said front area; and at least one of said connectors comprising a plug having a front portion fixed to one of said expander assemblies and a plug portion that extends vertically and has a taper complementary to said vertical slot of said at least one of said receptors.

6. The mandibular distraction device of claim 4, wherein:

at least one of said receptors comprises a back portion fixed to at least one of said tooth engagement members and a front portion defining said connector guide, said connector guide comprising a vertically tapering front member having a pair of vertically extending flanges thereon defining spaces between said front portion and said at least one tooth engagement member and a vertical stop; and at least one of said connectors comprising a cap having a front portion fixed to one of said expander assemblies having a rear surface engageable with said front portion of said at least one of said receptors and channel members on said front portion of said cup that extend vertically and have a taper complementary to said vertically tapering front member of said at least one receptor, said front portion being engageable with said vertical stop.

7. The mandibular distraction device of claim 6, wherein:

said vertically extending flanges have secondary flanges extending therefrom toward said at least one of said tooth engagement members forming glue pockets adapted to receive glue for gluing said cap to said receptor.

8. The mandibular distraction device of claim 6, wherein:

said front portion of said at least one of said receptors has a vertical alignment hole extending therein from an upper surface thereof.

9. The mandibular distraction device of claim 6, wherein said cap has a slot extending horizontally across said front portion thereof at a lower end of said cap.

10. The mandibular distraction device of claim 6, wherein said back portion of said at least one of said receptors comprises horizontally extending tabs and said back portion is fixed to two of said tooth engagement members.

11. The mandibular distraction device of claim 4, wherein said receptors and said connectors are made of stainless steel and soldered to said tooth engagement members and said expander assemblies, respectively.

12. The mandibular distraction device of claim 1, wherein said tooth engagement members are stainless steel crowns.

13. The mandibular distraction device of claim 1, wherein said tooth engagement members are stainless steel bands.

14. The mandibular distraction device of claim 1, wherein each said expandable screw device comprises first and second body portions having aligned threaded holes extending therein and a threaded shaft engaging both said threaded holes.

15. The mandibular distraction device of claim 1, wherein each said set of tooth engagement members comprises a plurality of members aligned for disposition on the teeth of one side of the mandible, and each said expander assembly comprises a forward portion connected to some of said members of one said set of tooth engagement members and a rearward portion connected to the remainder of said members of the one said set of tooth engagement members, said forward and rearward portions being expandable relative to each other for separation of said some of said members from said remainder of said members.

16. The mandibular distraction device of claim 15, wherein said first set of tooth engagement members, having said first pair of expander assemblies thereon, are connected to said second set of tooth engagement members having said second pair of expander assemblies thereon at said forward portions of said expander assemblies.

17. The mandibular distraction device of claim 16, wherein said forward portions of said expander assemblies and said some of said tooth engagement members are connected to each other by a further expander assembly.

18. The mandibular distraction device of claim 4, wherein:

at least one of said receptors comprises a front portion defining said connector guide, said connector guide comprising a pair of vertically extending flanges, a vertical stop on said front portion, an intermediate portion extending from said front portion and a back portion extending from said intermediate portion and fixed to at least one of said tooth engagement members, said intermediate portion spacing said back portion from said front portion; and at least one of said connectors comprising a cap having a front portion fixed to one of said expander assemblies, a rear surface engageable with said front portion of said at least one of said receptors and channel members on said front portion of said cap for engagement with said flanges, said front portion of said cap being engageable with said vertical stop.

19. The mandibular distraction device of claim 1, wherein each of said first and second pairs of expander assemblies comprises a single said expander screw device on one of said opposite sides of the respective said set of tooth engagement members and an expendable tube and pin slider device on the other of said opposite sides of the respective said set of tooth engagement members.

20. A mandibular distraction device, comprising:

first and second sets of tooth engagement members adapted to be attached to the bicuspid and molar teeth of respective opposite lateral sides of the mandible, wherein each of said first and second sets of tooth engagement members has opposite sides, and wherein each of said first and second sets of tooth engagement members comprises bicuspid engagement members and molar engagement members;

a first pair of expander assemblies removably attached to said opposite sides of said first set of tooth engagement members, said first pair of expander assemblies comprising at least one expander screw device;

a second pair of expander assemblies attached to said opposite sides of said second set of tooth engagement members, said second pair of expander assemblies also comprising at least one expander screw device;

bicuspid receptors attached to said bicuspid engagement members and molar receptors attached to said molar engagement members;

connectors attached to said first and second pairs of expander assemblies, said connectors being removably engaged with said receptors.

21. The mandibular distraction device of claim 20, wherein:

each of said receptors comprises a metal member fixed to at least one of said tooth engagement members and has a connector guide extending substantially perpendicular to the direction of expansion of one of said expander assemblies connected thereto; and each of said connectors comprises a metal member fixed to one of said expander assemblies and has an engagement surface complementary to said connector guide of a respective one of said receptors for removable engagement therewith in a direction substantially perpendicular the direction of expansion.

22. The mandibular distraction device of claim 21, wherein:

at least one of said bicuspid receptors comprises a front portion defining said connector guide, said connector guide comprising a pair of vertically extending flanges, a vertical stop on said front portion, an intermediate portion extending from said front portion and a back portion extending from said intermediate portion, said intermediate portion spacing said back portion from said front portion, and said back portion being connected with two of said bicuspid engagement members;

at least one of said molar receptors comprises a back portion fixed to two of said molar engagement members and a front portion defining said connector guide, said connector guide having a pair of vertically extending flanges thereon, and a vertical stop; and said connectors comprising a cap having a front portion fixed to one of said expander assemblies, a rear surface engageable with said front portion of said at least one of said receptors and channel members on said front portion of said cap for engagement with said flanges, said front portion of said cap being engageable with said vertical stop.

23. An assembly kit for a mandibular distraction device comprising:

first and second sets of tooth engagement members adapted to be attached to the bicuspid and molar teeth of respective opposite lateral sides of the mandible, wherein each of said first and second sets of tooth engagement members has opposite sides, and wherein each of said first and second sets of tooth engagement members comprises bicuspid engagement members and molar engagement members;

a first pair of expander assemblies that are removably or fixedly attachable to said opposite sides of said first set of tooth engagement members, said first pair of expander assemblies comprising at least one expander screw device;

a second pair of expander assemblies that are removably or fixedly attachable to said opposite sides of said second set of tooth engagement members, said second pair of expander assemblies also comprising at least one expander screw device;

bicuspid receptors attachable to said bicuspid engagement members and molar receptors attachable to said molar engagement members; and connectors attachable to said first and second pairs of expander assemblies, said connectors being removably fixedly engageable with said receptors.

* * * * *